United States Patent
Friberg et al.

(10) Patent No.: US 7,069,963 B2
(45) Date of Patent: Jul. 4, 2006

(54) MACHINE FOR VOLUMETRIC FILLING OF POWDERS

(75) Inventors: Claes Friberg, Åkers Styckebruk (SE); Lars Kax, Nykvarn (SE)

(73) Assignee: Mederio AG, Hergiswid (CH)

(*) Notice: Subject to any disclaimer, the term of this patent is extended or adjusted under 35 U.S.C. 154(b) by 310 days.

(21) Appl. No.: 10/777,682

(22) Filed: Feb. 13, 2004

(65) Prior Publication Data

US 2005/0173552 A1    Aug. 11, 2005

(30) Foreign Application Priority Data

Feb. 9, 2004    (SE) .................................... 0400282

(51) Int. Cl.
*B65B 1/04*    (2006.01)
(52) U.S. Cl. ............... 141/2; 141/18; 141/67; 141/71
(58) Field of Classification Search .............. 141/2, 141/18, 65, 67, 71, 98, 129, 144, 286
See application file for complete search history.

(56) References Cited

U.S. PATENT DOCUMENTS

| | | | | |
|---|---|---|---|---|
| 6,048,806 A | * | 4/2000 | Deeb et al. ................. | 442/151 |
| 6,403,216 B1 | * | 6/2002 | Doi et al. .................... | 428/364 |
| 6,581,650 B1 | * | 6/2003 | Parks et al. .................... | 141/12 |

* cited by examiner

*Primary Examiner*—Steven O. Douglas
(74) *Attorney, Agent, or Firm*—Oblon, Spivak, McClelland, Maier & Neustadt, P.C.

(57) ABSTRACT

The invention discloses a method and a tool for exact metering and volumetric filling of finely divided dry powder medicament doses into preformed containers, whereby the doses and containers are adapted for administration by inhalation using a dry powder inhaler (DPI). A filling tool illustrating the invention includes at least one receptacle (10). The shape and size of a receptacle may vary depending on the size and mass of the powder load to be metered. A stretched woven filter (106) is positioned between the second opening of the receptacle (10) and a suction nozzle (13), using flexible seals at joints to stop air and powder leakage. The shape may be circular or elliptical, the wideness and depth, i.e. the volume, is adapted to the intended load and the method of filling and unloading.

22 Claims, 5 Drawing Sheets

MACHINE FOR VOLUMETRIC FILLING OF POWDERS

TECHNICAL FIELD

Figure 1:
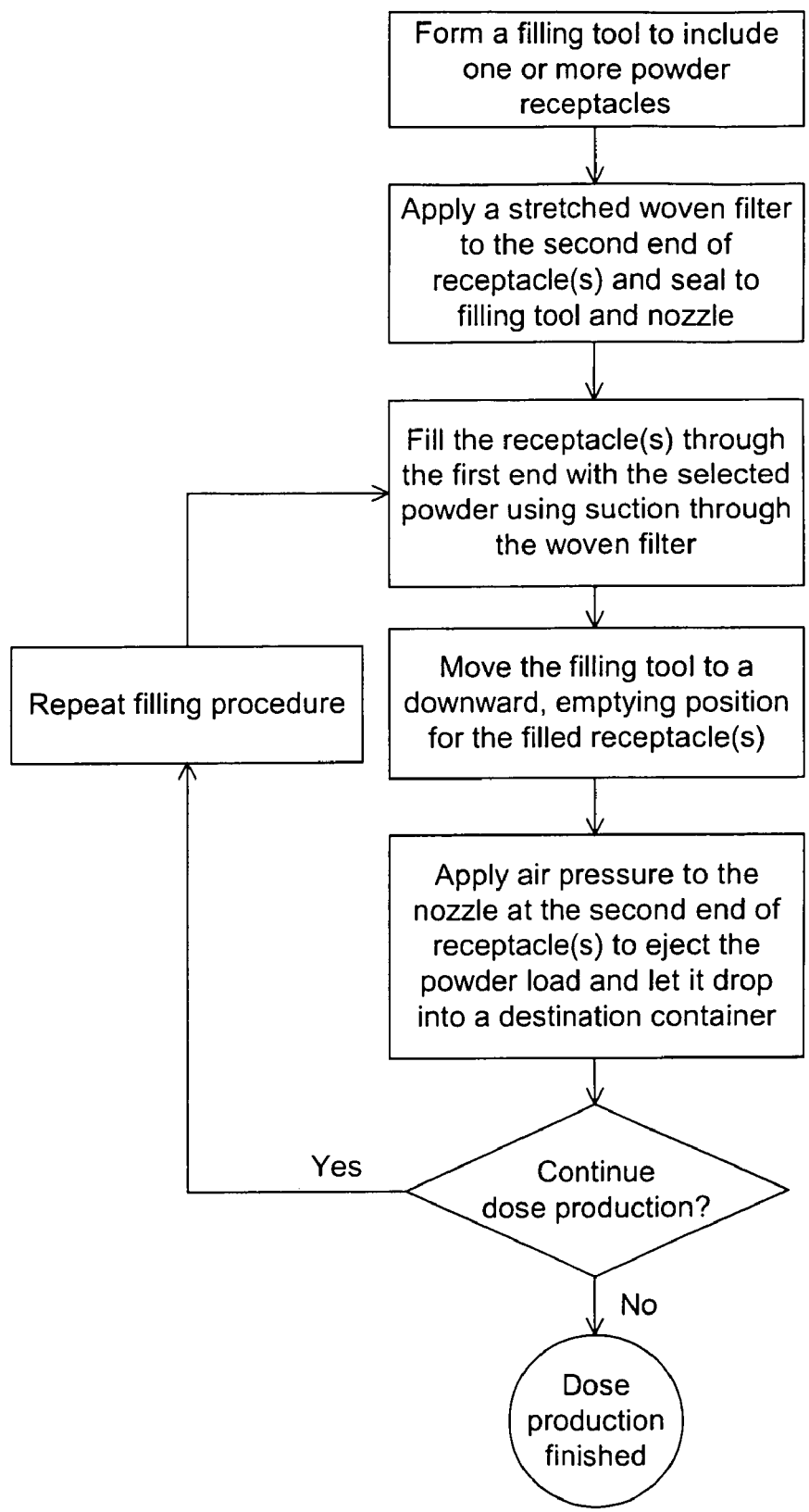
Figure 2:
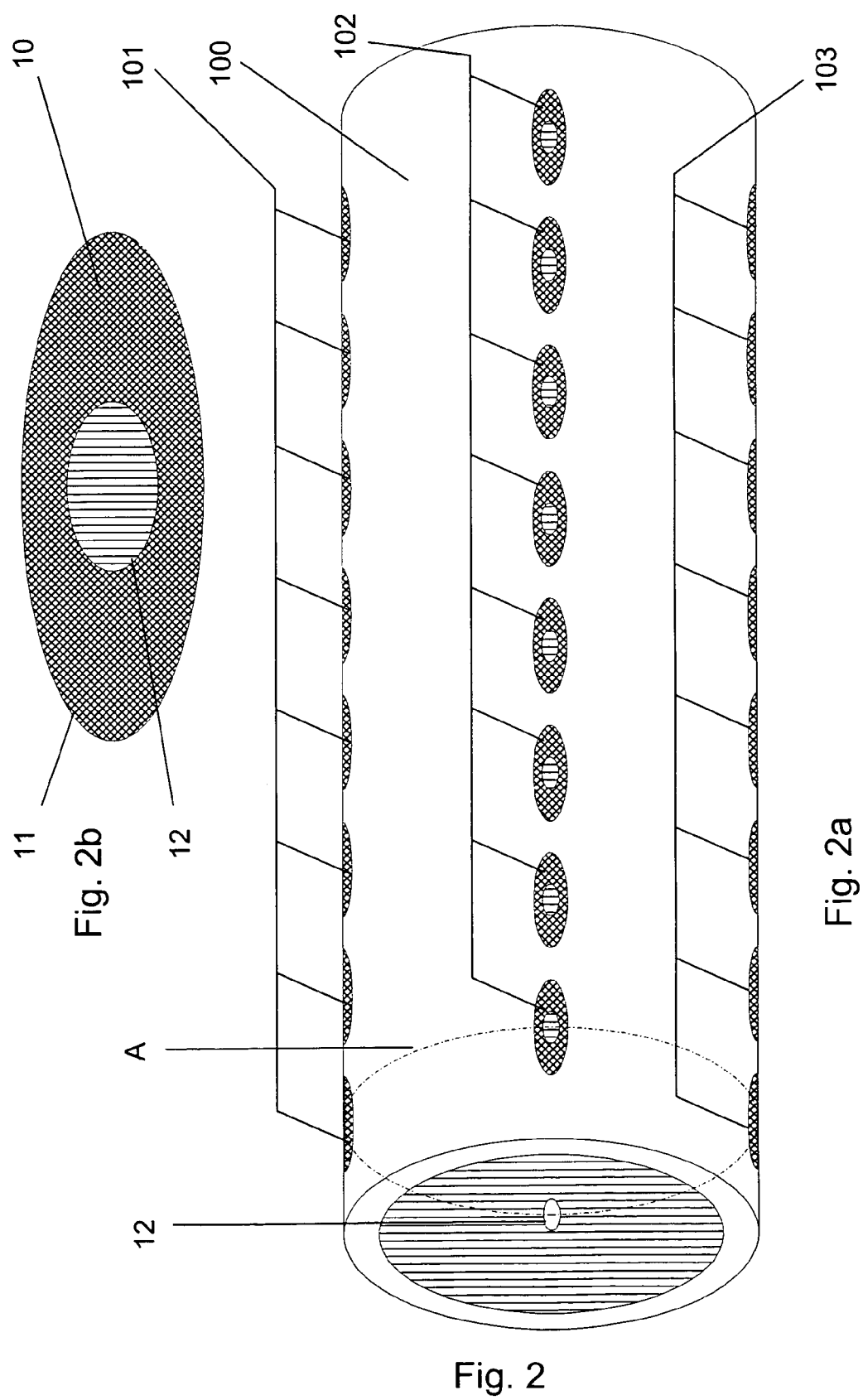
Figure 3:
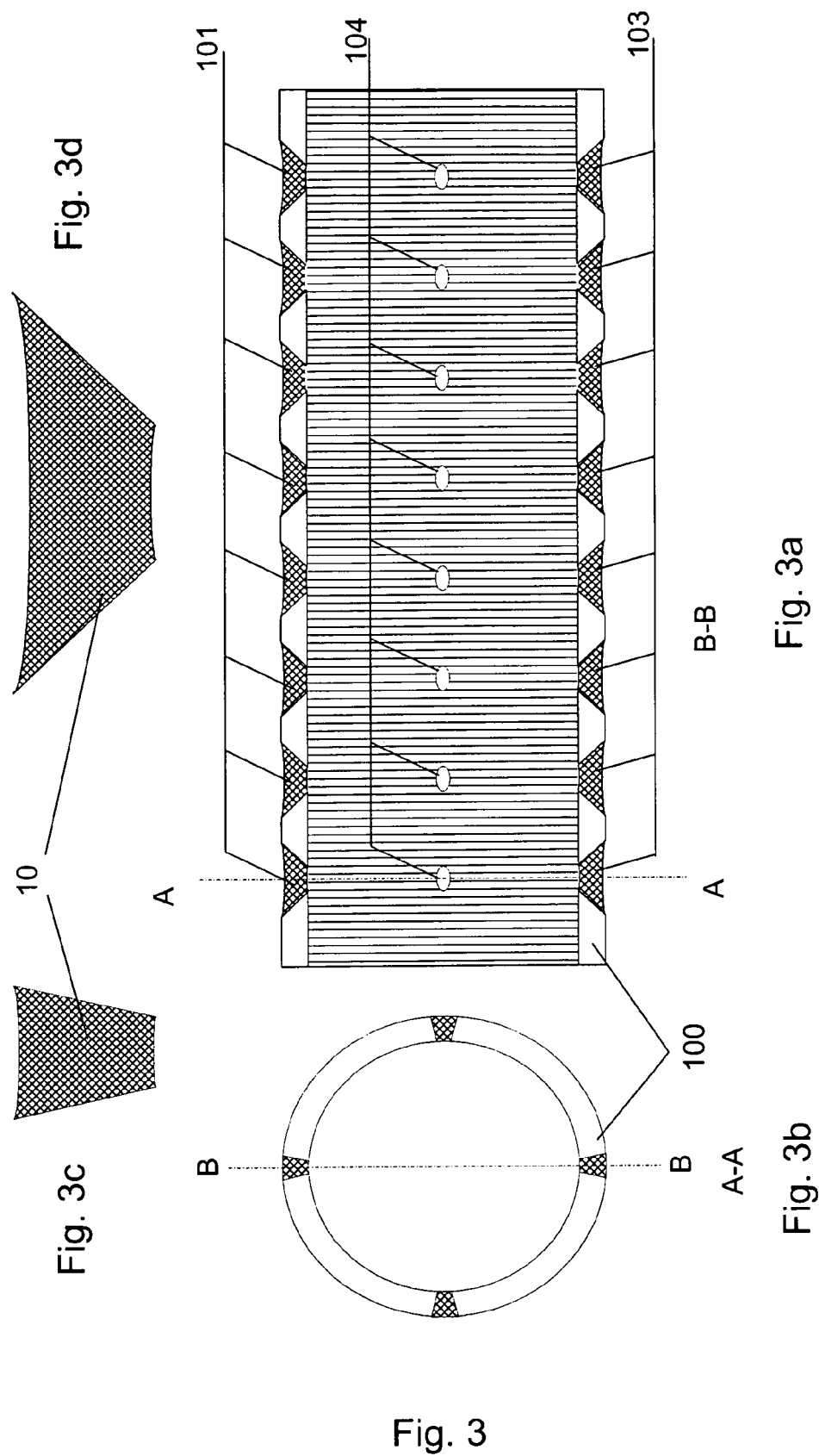
Figure 4:
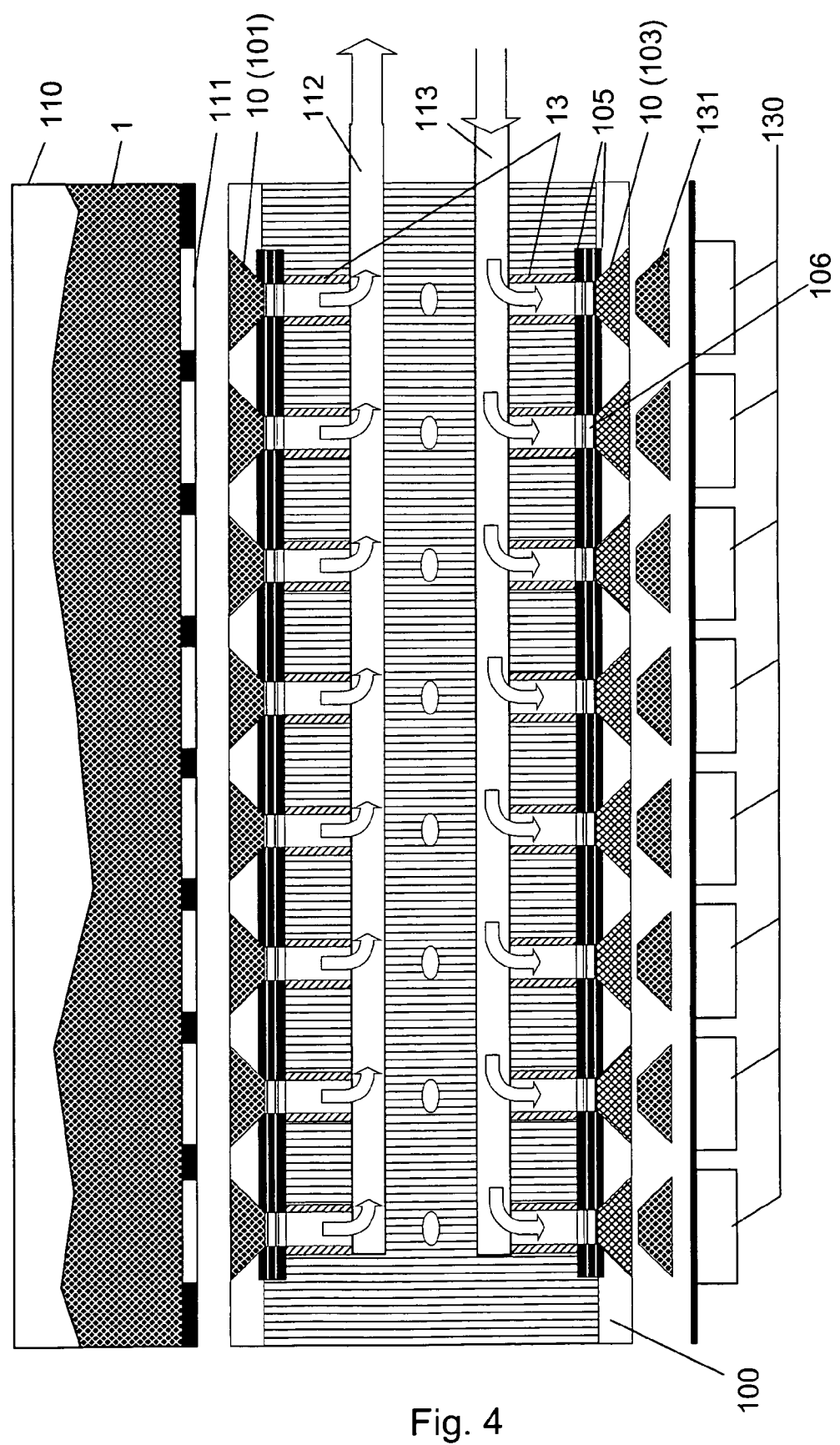
Figure 5:
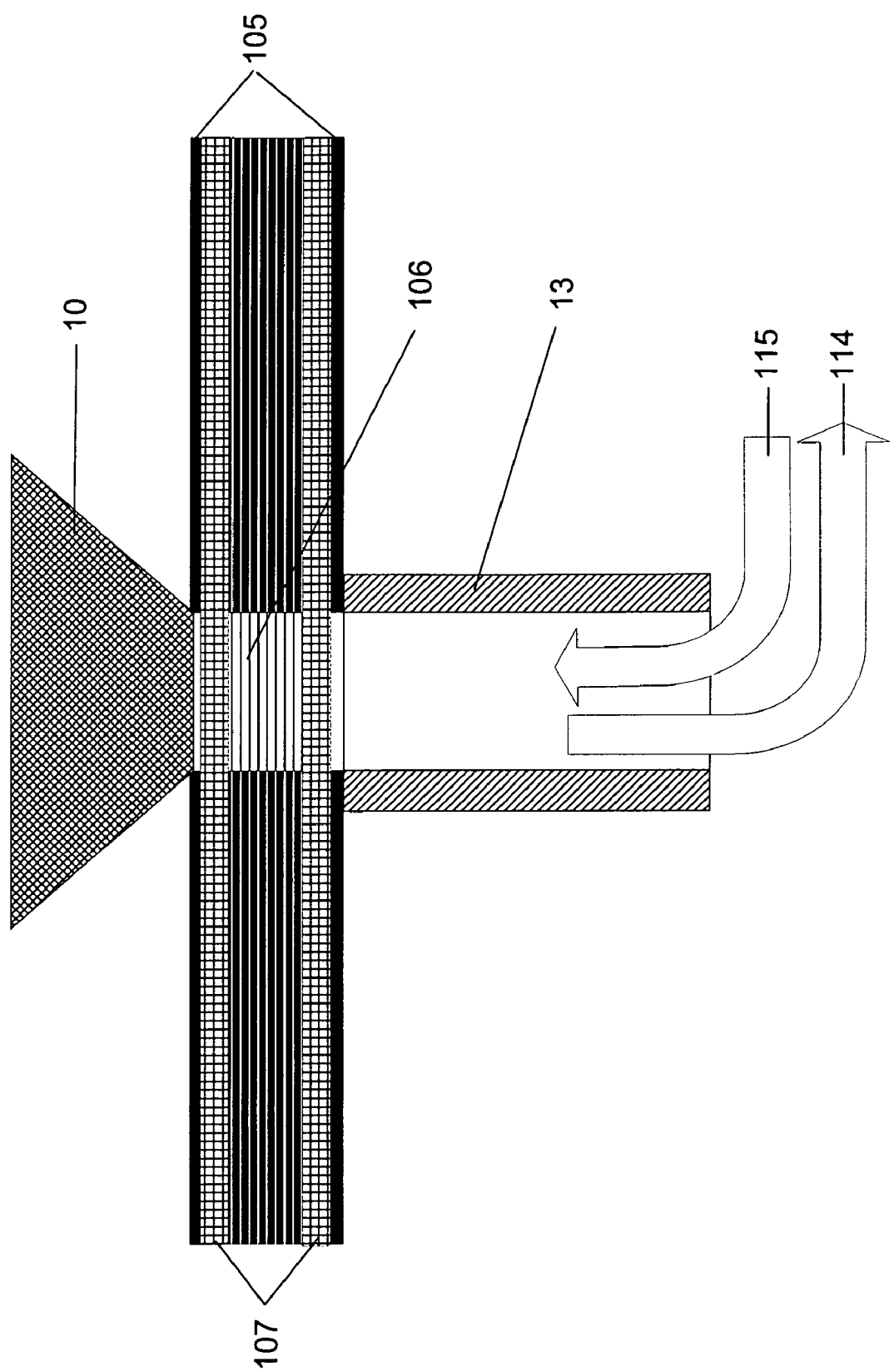

The present invention relates to a method and a device for filling a succession of containers with metered doses of finely divided dry medication powder, the doses intended for inhalation by means of a dry powder inhaler (DPI).

BACKGROUND

Dosing of drugs is carried out in a number of different ways in the medical service today. Within health care there is a growing interest in medical products based on administering drugs by inhalation of dry medicament powder directly to the airways and lungs of a patient. Interest focuses often on dry powder inhalers (DPI) because they offer effective, quick and user-friendly delivery of many substances formulated as dry powder doses for treatment of many different disorders. Because onset is faster and the efficacy of inhaled doses often are much higher than e.g. orally administered capsules or tablets, the inhalation doses need only be a fraction of the medicament powder mass in an oral capsule or tablet. Thus, there is an increasing demand for relatively low mass, inhalable, metered medicament doses, which require better filling methods and devices for making small and exact inhalation doses with low relative standard deviation (RSD).

Volumetric filling is by far the most common method of producing dry powder doses of medication drugs. Normally in a first step a quantity of powder is introduced into a receptacle of specified volume by gravitation, often aided by mechanical energy in the form of impaction or vibration, or the receptacle may be filled by suction force. Then in a second step, after stripping of possible surplus powder, the receptacle is moved to an emptying position, where the powder is unloaded from the receptacle by gravitation into a container such as a blister or capsule etc. A plurality of receptacles may be arranged in some kind of tool, which is adapted to a mechanism bringing a plurality of containers, e.g. blisters or capsules, in line with corresponding receptacles so that all doses of powder may be unloaded into the containers, one container per dose. The receptacle tool may be integrated into a filling machine such that the receptacles can be filled and emptied in a more or less continuous, cyclic fashion. Examples of prior art may be studied for instance in publications EP 0 319 131 B1, WO 95/21768, U.S. Pat. No. 5,826,633, U.S. Pat. No. 6,267,155 B1, U.S. Pat. No. 6,581,650 B2 and DE 202 09 156 U1.

Powders for inhalation need to be finely divided so that the majority by mass of particles in the powder is between 1 and 5 µm in aerodynamic particle size (AD). Powder particles larger than 5 μm tend not to deposit in the lung when inhaled, but to stick in the mouth and upper airways, where they are medicinally wasted and may even cause adverse side effects. However, finely divided powders are rarely free flowing, but are prone to adhere to all surfaces they come in contact with and the small particles tend to aggregate into lumps. This makes the metering of correct doses more difficult, since the bulk density of the powder may vary considerably from dose to dose even if the bulk density is constant when measured on powder quantities several magnitudes larger than the doses. Metering and filling correct quantities into a dose container is therefore more difficult with low dose masses. However, demand for doses from 5 mg down to 0.1 mg is increasing, putting pressure on the industry to improve methods and devices for metering and filling in the manufacturing stage as well as on dry powder inhalers to improve performance in terms of deaggregation and efficacy. Compacting the powder in the metering receptacle to reduce metering errors can be done, but care must be exercized so that agglomeration is not aggravated and to ensure that the agglomerates may still be de-aggregated by the inhaler.

Electrostatic forces, friction forces and van der Waal forces acting on particles become stronger than the gravitation force when particle size diminishes. Medication powders are very susceptible to electrostatic charging during transportation and handling of powders, especially in dry conditions. It is often necessary to remove as much as possible of electric charges of the particles by electric de-charging methods, particularly if the particles are small in size, in order to reduce the tendency of particles to stick to all surfaces of the handling equipment.

There is a need for improvements in methods and devices for precise metering of medicament doses of finely divided powders for inhalation and consistent, reliable filling of doses into suitable containers for use in inhaler devices.

SUMMARY

The present invention discloses a method and a device for precise, repeatable filling of finely divided dry powder into preformed containers; the container and the contained dose being adapted for inhalation by means of a DPI.

In a preferred embodiment of the invention woven filters are used together with elastic seals and optional supporting wire netting in connection with a multitude of metering receptacles for improving dose metering accuracy and dose forming reliability and for reducing powder retention in the metering receptacles.

In another aspect of the invention a filling tool is disclosed presenting a multitude of metering receptacles where at least the surface in the receptacles and optionally other tool parts are polished and if necessary specially coated to reduce friction and potential wear between the filling tool and associated parts. Appropriate polishing and coating may reduce the amount of powder sticking to the outer surface area of the filling tool during the filling operation and to the receptacle inner walls and other areas of the filling tool after unloading.

In yet another aspect of the invention the metering receptacles may be circular or elliptical cones with circular or oval openings towards the air supply. The elliptical form is preferred, because it may be adapted to fit an elongated, preformed container receiving a load from the conical receptacle, such that the powder load may be deposited onto the intended target area without spillage onto other areas of the container. The elastic seal around the opening in the conical metering receptacle for the air supply ensures a repeatable, leak-free connection between the opening, the filter and an air nozzle for many filling and unloading cycles.

In a further aspect of the invention the shape of the deposited load of powder, which may be a dose, is reduced in height by exposing the load or the load and container to an energy source such that the deposited powder load is reduced in height and distributed reasonably evenly over the available target area in the container before it is sealed, e.g by foiling. The energy supplied may be mechanical, e.g. ultrasonics, vibration or shock, or electric, e.g. static electricity or from an ac electric field.

In yet a further aspect of the invention the powder particles are electrically discharged by applying static charge elimination devices where needed to keep static charging to a minimum of the powder, the filling tool and associated equipment throughout the filling procedure. For instance, bulk powder in a metered load will be electrically discharged, i.e. electrically neutralized, the moment the powder load is unloaded from the metering receptacle. A source of electric charges, e.g. an ion source, may be installed in the gap existing between the tool and the containers, such that emitted electric charges from the ion source are attracted to electrically charged particles in the powder load while it transfers through air. Neutralizing electrically charged particles in this way eliminates particle spillage due to charged particles being electrostatically deflected in the direction of other objects and surfaces besides the intended target area of the container to be filled.

A volumetric filling method is set forth by the independent claim 1 and further embodiments are defined by the dependent claims 2 to 11 and a filling tool device is set forth by the independent claim 12 and further embodiments are defined by the dependent claims 13 to 22.

BRIEF DESCRIPTION OF THE DRAWINGS

The invention, together with further objects and advantages thereof, may best be understood by referring to the following detailed description taken together with the accompanying drawings, in which:

FIG. 1 illustrates in a flow diagram the filling method of the present invention;

FIG. 2(*a*) illustrates an embodiment of the filling tool and (*b*) illustrates an enlarged view of a conical receptacle;

FIG. 3(*a*) illustrates in principle a longitudinal section of an embodiment of the filling tool, (*b*) a cross section of the filling tool, (*c*) an enlarged view of cross section B and (*d*) an enlarged view of cross section A;

FIG. 4 illustrates in principle a longitudinal section of an embodiment of the filling tool together with the woven filter, the seals, the air nozzles, the air supply lines and the relative positions of the tool, the powder in a storage chamber with powder release chutes and the containers to be filled, and FIG. 5 illustrates in an enlarged view a cross section of a receptacle, seals, filter, optional wire netting and air nozzle;

DESCRIPTION OF THE INVENTION

The present invention discloses a method and a device for exact metering and volumetric filling of finely divided dry powder medicament doses into preformed containers, where the doses and containers are adapted for administration by inhalation using a dry powder inhaler (DPI). The method according to the present invention is illustrated in a flow diagram in FIG. 1.

In the context of the invention the term “container” is used generically and includes well-known designs such as blisters, capsules as well as bowls and pods, into which a metered quantity of dry powder medicament, a dose, may be deposited and sealed later to be made available in a DPI, which may deliver the dose as needed to a user inhaling through the DPI device. The term “receptacle” is used to describe a carefully made, truncated, conical cavity of very exact dimensions and volume—machined or otherwise made—into the outer surface of a filling tool, which may have more than one such cavity on its outer surfaces. From inside the tool access can be made to the smaller end of the conical cavity or cavities to allow fitting of filters and air supply nozzles, which will be described later.

Volumetric filling machines for dry powders in prior art are not easily adapted to metering and unloading of small doses, especially if the powder is finely divided presenting in the order of 90% by mass of particles with aerodynamic diameter between 1 and 5 μm. Gravitation in combination with impaction and vibration are popular prior art methods of first filling a receptacle and then unloading the powder collected in the receptacle into a selected container. Alternative methods and devices involving vacuum and air pressure to collect powder and fill it into targeted containers generally present better performance in terms of consistency and dose RSD compared to gravitation methods, especially when producing a dose of relatively small mass of powder particles less than 10 μm aerodynamic diameter. Excipients are commonly added to medicaments for different purposes, one of which is to dilute a potent medicament, another is to improve powder flowability.

A device according to the present invention is illustrated in FIGS. 2–5. FIG. 2 illustrates a filling tool 100 including four sets 101, 102, 103, 104 of eight receptacles 10 each. An enlarged top view 2(*b*) of a conical receptacle 10 is also illustrated showing a first 11 and a second 12 opening. The illustrated filling tool is a cylinder, but a different shape would also be possible, e.g. a part cylinder or a polygonal cross-section. The number of receptacles 10 in the tool 100 may vary depending on what capacity is required from the tool. The shape and size of a receptacle may vary depending on the size and mass of the powder load to be metered. The conical shape may be circular or elliptical, the wideness and depth, i.e. the volume, must be adapted to the intended load and the filling and unloading methods.

FIG. 3 illustrates in 3(*a*) a cross-section A—A and in 3(*b*) a cross section B—B of the filling tool. Enlarged cross-sections A 3(*d*) and B 3(*c*) of a receptacle 10 are also shown.

FIG. 4 illustrates a stylized, principal drawing of the operational filling tool 100 in a longitudinal cross-section together with a typical storage chamber 110 positioned above and in close proximity to the filling tool, a simple chute arrangement 111 for releasing powder 1 from the storage chamber to each individual receptacle 10 in set 101. A multitude of containers 130 are positioned beneath receptacles 10 of set 103 and just ejected loads 131 are in the air on their way to their respective containers. Also shown are flexible seals 105, woven filters 106, air nozzles 13 and connecting air lines 112 and 113 for suction 114 during filling and air pressure 115 during unloading, respectively. Separate airlines are shown in the embodiment to simplify the reader’s understanding of the principle, but in practice the same air line may be used alternately for suction and pressure during a complete sequence of filling and unloading.

FIG. 5 illustrates a stylized, principal, cross-sectional drawing of a receptacle 10, seals 105, woven filter 106, air nozzle 13 and optional wire netting 107 on one of the two or both sides of the filter in order to support it, if deemed necessary. Suction 114 and pressure 115 are also symbolically illustrated.

A filter is necessary when using air to attract or repel powder. A well-balanced suction force applied to a receptacle will attract available, nearby powder and will fill up the receptacle, such that the powder is compacted to a certain degree in the receptacle acting as a metering chamber. The filter at the bottom of the receptacle stops powder from being sucked into the air system and thereby becoming lost in the filling process. The filter is also necessary when air pressure is used to push the load out of the receptacle during the unloading operation, because it will stop possible foreign particles in the air supply system from contaminating the powder in the load. The filter should not be made of felt, because felt material may give off fibers, which may contaminate the powder load. Felt filters are usually rather thick and the fibers in the felt are not held in place by design; the felt is just a compressed collection of fibers, randomly arranged and held together by a bonding agent and a more or less loose fabric. In use the felt will let go of fibers, which may mix into the powder and follow the powder load into the container. The present invention preferably uses a woven, pre-stretched, surface-treated thin filter manufactured by W. L. Gore & Associates, Inc. of Newark Del., which by design cannot lose fibers to air passing through.

A further advantage of the invention is that the filter is so thin that it is easily sealed to the air connection end of the metering receptacle. Instead of common prior art practice of squeezing the felt filter tight to the receptacle by mechanical high force deforming the thick felt, the stretched woven filter is held in place by an elastic seal, which seals the filter to the bottom end of the receptacle, preferably using an arrangement comprising a resilient, moderate spring force acting on the air nozzle on the other side of the seal, whereby the contact pressure is kept constant, thus maintaining a tight connection between the air nozzle and the air connection end of the receptacle. The seals should be non-fibrous and may be made of e.g. PTFE, PFA, EPDM, Neoprene or Nitril and similar, medically approved materials. A further advantage of the invention is that the woven filter requires much less differential pressure across it compared to a felt filter for a given flow and particle filtration, i.e. less energy is needed, which simplifies control of the filling and unloading operations.

Proper metering of the powder quantity in the receptacle is difficult but important and consistency between loads out of the same receptacle is of course also important and so is consistency between loads from different receptacles in the same tool, if there are more than one. A prior art felt filter is easily deformed when it is squeezed tight to the air connection end of a receptacle, e.g. by pushing an air nozzle with considerable force into the felt. The felt will bulge inwards and intrude into the bottom of the metering receptacle, thus reducing the actual volume in the receptacle, which in turn reduces the powder load sucked into the receptacle in the filling step and results in lower powder mass in the load to be transferred to a receiving container. The present invention solves this problem by using a pre-stretched, woven filter, which is not deformed by the moderate force needed to tighten the filter to the air connection end and it neither intrudes into the receptacle nor expands in the other direction, whereby the volume of the receptacle remains unaffected. Optionally a supporting wire netting may be used, if deemed necessary, to support the filter on one or both sides of the filter. The result is not only a reduced relative standard deviation (RSD) between subsequent loads from the same receptacle but also less RSD between loads from different receptacles. Of course a metered dose in a container may comprise more than one load, but this is by exception and not the normal procedure, because it takes longer time.

Each receptacle is lined up with and connected to a nozzle, which in turn is connected to a supply of vacuum and compressed air through at least one fast acting on-off valve. For the sake of simplicity, the valve(s) may be common to all nozzles. Filling the receptacles is accomplished by making powder available to the receptacles, e.g. through a chute arrangement from a storage chamber, such as a trough or a hopper. Normally powder is fed by gravitation, optionally aided by addition of energy, e.g. by vibrating the trough. When the tool containing the receptacle(s) has brought at least one receptacle in position to be filled, by opening of at least one valve, suction is applied from a vacuum source to the respective air nozzle, which in turn sucks powder and compacts the load to a degree into the corresponding receptacle. The woven filter stops powder from entering the nozzle. After completing filling of some or all receptacles of the filling tool, the tool is cleaned from surplus powder and moved to a downward pointing position for unloading the load of at least one receptacle into a selected container. When a valve opens, a pulse of compressed air is led through at least one nozzle and filter to the at least one receptacle, where the air exerts a force on the powder load in the receptacle. The load will be ejected from the receptacle and will drop into a selected container, provided it is in correct position. If the tool contains a plurality of receptacles it is advantageous to control the channeling of compressed air to the receptacles one by one in turn. In doing so the risk of dropping air pressure during unloading is eliminated, which may otherwise cause problems if the air pulse is channelled simultaneously to all receptacles, since the individual loads are unlikely to leave their respective receptacles at exactly the same moment. This problem of synchronization may lead to higher powder retention in some receptacles, which are late in releasing their loads.

Surprisingly, it has been found that the retention of powder in the metering receptacle after unloading is less when using the woven filter compared to the felt ditto. The reason for this is that because the felt filter of prior art becomes quite deformed and quite dense around the edges, where it is kept tight to the air connection end, pressurized air may only pass through with great difficulty near the inner wall of the receptacle during the ejection of the load. This phenomenon leads to a substantially reduced air stream near the receptacle inner wall with insufficient turbulence to clean out all of the powder adhering to the wall. However, even when the woven filter is used instead of the felt filter the cone angle of the receptacle should not be too great, otherwise there is a risk that powder retention on the inner walls of the receptacle increases due to insufficient air turbulence near the wall.

Reducing powder retention on all surfaces that may come in contact with powder is a further aspect of the present invention. The material of the filling tool must be carefully selected to present extreme stability of form, good machining properties, good resistance to abrasion, high surface finish with low friction properties, if necessary achieved by coating. Suitable materials for the filling tool include for instance vacuum-arc-remelted (VAR) stainless steel, metals, alloys and glass. Suitable coating materials may be selected from thermoplastic materials, such as PTFE, PE, parylene and similar. The tool surfaces in contact with powder, e.g. the metering receptacles, should be polished or coated to a fineness modulus of less than $R_a$=0.25 μm, and preferably less than $R_a$=0.1 μm and the resulting surface should present as low dynamic friction coefficient as possible. A preferred embodiment of the filling tool uses a machined stainless steel body, which is ground in several steps and then optionally electro-polished, which results in a fineness of less than $R_a$=0.1 μm. The filling tool may then be metallurgically coated by vapour deposition of e.g. chromium nitride, coal/chrome-combination or graphitic coating. This will ensure a durable filling tool surface with very low friction, making it easy to remove sticking powder particles. Naturally, consideration must be paid to the type of medicament powder and powder formulation in deciding what materials to use for the filling tool, the appropriate grinding and polishing steps and type of coating, if needed.

Electrostatics is often a problem in handling of dry powders, especially finely divided powders. Fine particles are easily triboelectrically charged when transported, not only by contact with objects of the transportation system but also by flowing air. The problem is aggravated by the necessity of handling the powder in a dry atmosphere, typically below 20% relative humidity, in order not to affect the quality and properties of the powder. The powder particles may be electrically discharged by applying static elimination devices, e.g. from NRD LLC, Grand Island, N.Y., where needed to keep static charging of the powder, the filling tool and associated equipment to a minimum throughout the filling procedure. By doing so loss of particles due to particle-sticking and other interference from statics with the filling process are kept to a minimum. When an applied air pressure pulse unloads the powder load from the metering receptacle, the powder particles must pass an existing air gap before reaching a receiving container. By triboelectric charging, particles aquire a positive or negative charge to a higher or lesser extent. This electric charge makes them disposed by the influence of stray electric fields, existing in the air gap, to deflect in other directions than the expected inertial and gravitational track and thus settle onto other surface areas than the expected target area of the receiving container. To reduce spillage of this sort the present invention discloses the addition of a source of neutralizing charges, e.g. an ion source, to be positioned near the air gap between the tool incorporating metering receptacle(s) and the container(s). Electrically charged particles will then very quickly be neutralized by charges from the source and the loss of particles in transfer from receptacle to container due to electrostatics will be reduced.

When the powder load from the receptacle has been deposited in the container it may be necessary to spread the powder load more evenly over the available area inside the still open container, if the deposit has developed powder peaks. The peaks may interfere with a sealing cover, e.g. a foil to be applied on top of the container in order to seal the container in a next step. Spreading the powder may be accomplished in many ways, but preferably without means that presume contact between means and powder, e.g. scrapers. Preferred embodiments of spreading means include a vibrating or shock arrangement to jar the container, or ultrasonics to upset the powder so that powder peaks will collapse and not interfere with the seal being put onto the container in an ensuing step.

The present invention relates to consistent filling of dry powder doses of medicament into containers destined for insertion into a DPI, where the pre-metered doses are in a range 100 μg–50 mg and preferably in a range 100 μg–10 mg and most preferably in a range 100 μg–5 mg and presenting an RSD of 5% or less.

What has been said in the foregoing is by example only and many variations to the disclosed embodiments may be obvious to a person of ordinary skill in the art, without departing from the spirit and scope of the invention as defined in the appended claims.

The invention claimed is:

1. A volumetric method of consistent metering and filling of doses of finely divided dry powder medicaments into containers, characterized by the steps of forming a filling tool to include at least one powder receptacle having a first opening and a second opening, the receptacle having a volume corresponding to a chosen load mass of a selected medicament powder, the load representing at least a part-dose and preferably representing a dose;

applying a stretched woven filter between the second opening of the receptacle and a suction nozzle, using flexible seals at joints to stop air and powder leakage, whereby distortion and variation of the receptacle volume is prevented during a filling operation and where the woven filter eliminates a risk of loose filter fibers getting mixed with the powder load;

filling the at least one receptacle with the selected medicament powder from a storage chamber using suction power through the woven filter, whereby a powder load of known mass is formed by the assistance of the woven filter;

moving the filling tool to a new position such that the at least one receptacle, now filled with a powder load, is brought in a downward facing, emptying position;

applying air pressure to the second opening of the receptacle such that the load is ejected and directed towards a container positioned beneath the receptacle, whereby at least a part-dose or preferably the dose is formed in the container; and repeating the steps of filling the receptacle, moving the filling tool and applying air pressure, whereby doses are produced in a multitude of containers, the doses having a relative dose-to-dose standard deviation below 10% and preferably below 5%.

2. The method according to claim 1, characterized by the further step of re-enforcing the mechanical strength of the woven filter by arranging a supporting wire netting at one or optionally both sides of the woven filter.

3. The method according to claim 1, characterized by the further step of selecting a filling tool material providing selected properties regarding stability of form, machining, resistance to abrasion and low friction in a group of materials comprising stainless steel, metals, alloys and glass.

4. The method according to claim 1, characterized by the further step of applying a hard-wearing, low-friction coating onto at least surfaces of the receptacles in the filling tool, optionally on other surfaces of the same, thereby reducing the dynamic friction and powder retention susceptibility of exposed surfaces and making cleaning easier.

5. The method according to claim 1, characterized by the further step of applying a spring force to keep contact pressure constant between an air nozzle, the filter and the second opening of the respective receptacle, such that elastic seals sealing nozzle, filter and receptacle will stop leakage of air and powder into and out of the receptacle.

6. The method according to claim 1, characterized by the further step of making the shape of the at least one receptacle of the filling tool to an elliptic form in order to adapt the physical form of the powder load to fit a pre-defined elongated form of a container, which will receive the load upon unloading from the receptacle.

7. The method according to claim 1, characterized by the further step of arranging a source of electric charges, preferably an ion source, in an air gap between the filling tool and the container(s) such that electrically charged particles in ejected powder loads become electrically neutralized while being transferred through the air.

8. The method according to claim 1, characterized by the further step of arranging sources of electric charges, preferably ion sources, at a working distance to the filling tool and optionally at a working distance to the powder in a storage chamber in order to accomplish that electrostatic charges on the tool and associated equipment and powder particles in the storage become electrically neutralized such that the filling process is not adversely affected.

9. The method according to claim 1, characterized by the further step of reducing the height of a deposited powder load in a destination container by subjecting the load, or the container and load, to an energy source, which may be ultrasonic, vibrating, shocking or electrical in nature, such that the load is spread out inside the container and cannot interfere with a cover, preferably a sealing foil, in an ensuing sealing procedure.

10. The method according to claim 1, characterized by the further step of reducing the height of a deposited powder load in a destination container by subjecting the load, or the container and load, to a doctor blade such that the load is spread out inside the container and cannot interfere with a cover, preferably a sealing foil, in an ensuing sealing procedure.

11. The method according to claim 1, characterized by the further step of choosing the load mass of the selected medicament powder to be in a range 100 µg–50 mg and preferably in a range 100 µg–10 mg and most preferably in a range 100 µg–5 mg.

12. A filling tool device for consistent, precise, repeatable metering and filling of doses of finely divided dry powder medicaments into containers, characterized in that the filling tool is arranged to comprise at least one powder receptacle having a first and a second opening, the receptacle being of a volume corresponding to a chosen load mass of a selected medicament powder, the load representing at least a part-dose or preferably representing a dose;

a stretched, form-stable, woven filter is applied between the second opening of the receptacle and a suction nozzle, and flexible seals are being used at joints to stop air and powder leakage, the woven filter preventing distortion and variation of the receptacle volume during a filling operation and eliminating a risk of loose filter fibers getting mixed with the powder load;

the at least one receptacle is filled with the selected powder from a storage chamber by suction power through the woven filter, whereby a consistent powder load mass is formed by the assistance of the form-stable, woven filter;

the filling tool is moved to an emptying position and air pressure of sufficient power is applied to the second opening of the receptacle such that the load may be ejected in a direction towards a container positioned beneath the receptacle, whereby at least a part-dose and preferably the dose is deposited into the container, and the steps of filling the receptacle, moving the filling tool and applying air pressure are repeated, whereby doses are deposited in a multitude of containers, the doses having a relative dose-to-dose standard deviation below 10% and preferably below 5%.

13. The filling tool device according to claim 12, characterized in that the mechanical strength of the woven filter is re-enforced by arranging a supporting wire netting at one or optionally both sides of the woven filter.

14. The filling tool device according to claim 12, characterized in that a filling tool material is selected providing appropriate properties regarding stability of form, machining, resistance to abrasion and low friction from a group of materials comprising stainless steel, metals, alloys and glass.

15. The filling tool device according to claim 12, characterized in that a hard-wearing, low-friction coating is applied to at least surfaces of the receptacles in the filling tool, optionally to other surfaces of the same, thereby reducing the dynamic friction and powder retention susceptibility of exposed surfaces and making cleaning easier.

16. The filling tool device according to claim 12, characterized in that a spring force is applied to keep contact pressure constant between an air nozzle, the filter and the second opening of the respective receptacle, such that elastic seals sealing nozzle, filter and receptacle will stop leakage of air and powder into and out of the receptacle.

17. The filling tool device according to claim 12, characterized in that the shape of the at least one receptacle of the filling tool is made to an elliptic form in order to adapt the physical form of the powder load to fit a pre-defined elongated form of a container, which will receive the load upon unloading from the receptacle.

18. The filling tool device according to claim 12, characterized in that a source of electric charges, preferably an ion source, is arranged in an air gap between the filling tool and the container(s) such that electrically charged particles in ejected powder loads become electrically neutralized while being transferred through the air.

19. The filling tool device according to claim 12, characterized in that sources of electric charges, preferably ion sources, are arranged at a working distance to the filling tool and optionally at a working distance to the powder in a storage chamber in order to accomplish that electrostatic charges on the tool and associated equipment and powder particles in the storage become electrically neutralized such that the filling process is not adversely affected.

20. The filling tool device according to claim 12, characterized in that the height of a deposited powder load in a destination container is reduced by subjecting the load, or the container and load, to an energy source, which may be ultrasonic, vibrating, shocking or electrical in nature, such that the load is spread out inside the container and cannot interfere with a cover, preferably a sealing foil, in an ensuing sealing procedure.

21. The filling tool device according to claim 12, characterized in that the height of a deposited powder load in a destination container is reduced by subjecting the load, or the container and load, to a doctor blade such that the load is spread out inside the container and cannot interfere with a cover, preferably a sealing foil, in an ensuing sealing procedure.

22. The filling tool device according to claim 12, characterized in that the load mass of the selected medicament powder is chosen to be in a range 100 µg–50 mg and preferably in a range 100 µg–10 mg and most preferably in a range 100 µg–5 mg.

* * * * *

UNITED STATES PATENT AND TRADEMARK OFFICE
CERTIFICATE OF CORRECTION

PATENT NO. : 7,069,963 B2 Page 1 of 1
APPLICATION NO. : 10/777682
DATED : July 4, 2006
INVENTOR(S) : Claes Friberg et al.

It is certified that error appears in the above-identified patent and that said Letters Patent is hereby corrected as shown below:

On the title page, Item (73), the Assignee city is incorrect. Item (73) should read:

-- (73)　　Assignee:　　Mederio AG, Hergiswil (CH) --

Signed and Sealed this

Seventh Day of November, 2006

JON W. DUDAS
*Director of the United States Patent and Trademark Office*